(12) United States Patent
Hawkins

(10) Patent No.: US 8,821,448 B2
(45) Date of Patent: Sep. 2, 2014

(54) APPARATUS FOR SEALING, SECURING AND ADJUSTING THE LENGTH OF A FLEXIBLE TUBE

(76) Inventor: Charles R. Hawkins, Bartlett, TN (US)

( * ) Notice: Subject to any disclaimer, the term of this patent is extended or adjusted under 35 U.S.C. 154(b) by 855 days.

(21) Appl. No.: 12/267,552

(22) Filed: Nov. 7, 2008

(65) Prior Publication Data

US 2009/0125003 A1  May 14, 2009

Related U.S. Application Data

(63) Continuation-in-part of application No. 11/417,416, filed on May 4, 2006, now abandoned.

(51) Int. Cl.
*A61M 5/32* (2006.01)
*A61M 25/02* (2006.01)

(52) U.S. Cl.
CPC ......... *A61M 25/02* (2013.01); *A61M 2025/024* (2013.01); *A61M 2025/0293* (2013.01); *A61M 2025/028* (2013.01)
USPC ........................................................ 604/174

(58) Field of Classification Search
USPC .................... 604/174–175, 177; 128/DIG. 26
See application file for complete search history.

(56) References Cited

U.S. PATENT DOCUMENTS

| | | | |
|---|---|---|---|
| 3,938,529 A | 2/1976 | Gibbons | |
| 4,460,356 A | 7/1984 | Moseley | |
| 5,092,849 A * | 3/1992 | Sampson | 604/175 |
| 5,222,970 A | 6/1993 | Reeves | |
| 5,578,013 A | 11/1996 | Bierman | |
| 5,681,290 A * | 10/1997 | Alexander | 604/180 |
| 6,231,547 B1 * | 5/2001 | O'Hara | 604/174 |
| 6,819,951 B2 | 11/2004 | Patel et al. | |
| 2001/0049497 A1 | 12/2001 | Kalloo et al. | |
| 2003/0045862 A1 | 3/2003 | Jacobs et al. | |
| 2007/0016167 A1 | 1/2007 | Smith et al. | |

\* cited by examiner

*Primary Examiner* — Kevin C Sirmons
*Assistant Examiner* — Deanna K Hall
(74) *Attorney, Agent, or Firm* — Wyatt, Tarrant & Combs, LLP; William S. Parks

(57) ABSTRACT

An apparatus for sealing, securing and adjusting the length of a flexible tube is disclosed. The apparatus has a housing and an anchor. The housing has a sealing section, middle section and a opposing end. The housing has an outer surface and an inner lumen. The housing has at least one pair of abutted surfaces which define a slit from said outer surface to said lumen. The anchor has a base and a grip. The grip extends upwardly from the base. The grip is configured to engage the middle section of the housing. A method for using an apparatus for sealing, securing and adjusting the length of a flexible tube is also disclosed.

14 Claims, 4 Drawing Sheets

APPARATUS FOR SEALING, SECURING AND ADJUSTING THE LENGTH OF A FLEXIBLE TUBE

RELATED APPLICATIONS

This application is a continuation in part of application Ser. No. 11/417,416, May 4, 2006, now abandoned.

STATEMENT REGARDING FEDERALLY SPONSORED RESEARCH OR DEVELOPMENT

Not Applicable

REFERENCE A "MICROFICHE APPENDIX"

Not Applicable

FIELD OF THE INVENTION

The present invention is related to establishing a flexible tube insertion length in relation to its insertion site, securing it to the recipient proximal to the insertion site, sealing the insertion site and customizing the external length of the flexible tube if desired.

BACKGROUND OF THE INVENTION

The insertion of flexible tubes, such as catheters and cannulae, into a body cavity, duct or vessel to drain fluid or administer a substance such as a medication is a common medical procedure. A catheter, such as a peripherally inserted central catheter (PICC line), is a form of intravenous access that can be used for a prolonged period of time. A PICC is inserted in a peripheral vein and then advanced through increasingly larger veins, toward the heart until the tip rests in the superior vena cava or cavo-atrial junction.

PICCs are usually inserted by radiologists, physician assistants, radiologist assistants, or certified registered nurses. When inserting the PICC line, the physician or other medical personnel utilizes ultrasound, chest radiographs and fluoroscopy to aid in the insertion and to confirm placement. Placement of the distal end of the catheter at a predetermined location is important in order to achieve the desired therapeutic results. PICC lines generally will remain in place no longer than 30 days, although duration of use varies from just a few days in patients requiring short term treatments to a year for patients requiring longer treatment.

Tube or catheter placement in arterial and venous applications, such as the placement of PICC lines, is a common use of this invention. Other applications such as tube or catheter placement in organs or tube or catheter placement in certain body ducts or cavities to allow for fluid drainage will also benefit from this invention.

Devices to removably secure tubes or catheters to the recipient are known in the art. These range from gripping and securing devices for rigid needles to flexible tubes inserted after or while the entry is created. The securing devices range from simple wing on anchor designs to elaborately adjustable platforms. Securing these devices to the recipient is usually accomplished by stitching, pre-applied adhesive on the device, simply taping or a combination.

Although prior patents have advanced the art in both function and ease of use, none provide the simplicity of form and function addressed by the present invention.

BRIEF SUMMARY OF THE INVENTION

The present invention is related to establishing a flexible tube, namely a catheter or cannula, insertion length in relation to its insertion site, securing it to the recipient proximal to its insertion site, sealing the insertion site customizing its external length if desired. The invention allows the modification of the length of a flexible tube as needed to ensure proper placement of the tip of the tube within its recipient. A very high percentage of flexible tubes are placed within an existing lumen structure of a recipient. Normally the flexible tube or catheter is introduced into a lumen structure from a remote insertion site and passively or actively guided to the desired location. Once the distal tip is at the desired location of a lumen structure, the most common position fixing of the catheter is by externally securing it to the recipient thereby controlling its insertion length.

The invention discloses a sealing section which is partially inserted into the insertion site which in conjunction with the elasticity of surrounding tissue seals the insertion. The invention discloses a housing and an anchor which provide the means to removably secure the apparatus to the recipient. The exterior length of the catheter may be customized by cutting and attaching a connection end to the catheter, generally a hub receiver. In another embodiment, the opposite end of the housing is a hub receiver. Especially during long term use, the viability of the originally attached connection end which connects the catheter to fluid supply may need replacing. The customized exterior length may also leave some excess exterior length for cutting the old connection off and attaching a new connection end thereby minimizing the need to disturb the cannula or catheter.

This invention discloses an apparatus that allows for the adjustment of the inserted length of a flexible tube or catheter and then for the secure attachment of the flexbile tube proximal to the insertion site. The apparatus is self-sealing at the insertion site to prevent transmission of fluids or other matter into or out of the insertion site. The apparatus stabilizes the catheter at the insertion site to reduce tissue trauma, irritation, or enlargement of the insertion wound. The apparatus eliminates pistoning of the catheter at the insertion site which decreases the transmission of matter into or out of the insertion site thereby reducing the likelihood of infection and irritation.

The invention discloses a sealing section that may be tapered, smooth or stepped. The sealing section has an insertion end which is inserted into the tissue of a recipient of the cannula or catheter. The insertion end is inserted into the tissue sealing the insertion wound which minimizes tissue trauma. The insertion end does not protrude unnecessarily into the blood vessel or body tissue minimizing the chance of thrombus or other adverse effects.

The housing has at least one pair of abutted surfaces which define a slit.

BRIEF DESCRIPTION OF THE DRAWINGS

The present invention will be better understood by reference to the following detailed description when considered in conjunction with the accompanying drawings wherein.

DETAILED DESCRIPTION OF THE INVENTION

Figure 1:
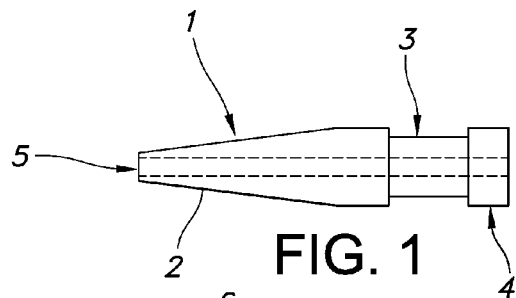
FIG. 1 is a schematic side view of a housing.
Figure 2:
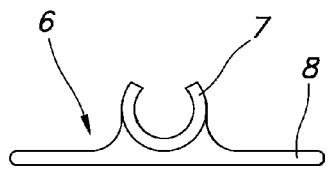
FIG. 2 is a schematic end view of an anchor.
Figure 3:
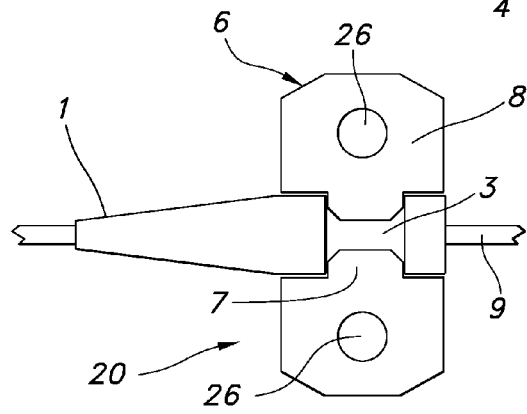
FIG. 3 is a schematic top view of an apparatus for sealing, securing and adjusting the length of a flexible tube.
Figure 4:
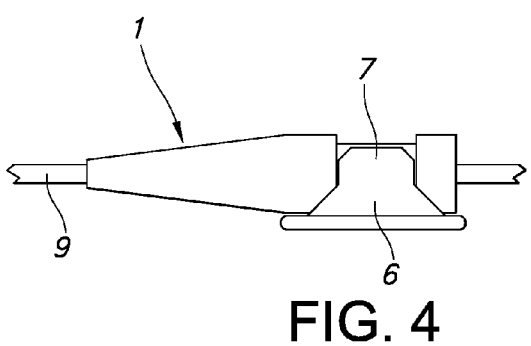
FIG. 4 is a schematic side view of an apparatus for sealing, securing and adjusting the length of a flexible tube.
Figure 5:
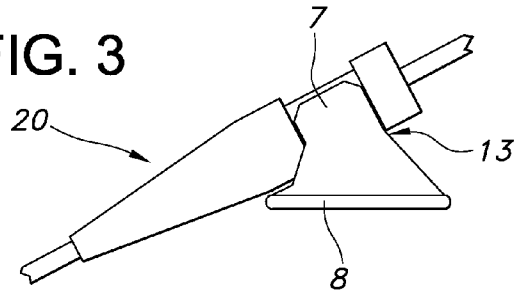
FIG. 5 is a schematic side view of an apparatus for sealing, securing and adjusting the length of a flexible tube wherein the grip extends upwardly from the base at an angle greater than 90°.

As used in this application, the term catheter refers to a hollow, flexible tube inserted into a body cavity, duct or vessel to allow the passage of fluids or distend a passageway. As used in this application, the term cannula refers to a flexible tube that is inserted into a bodily cavity, duct or vessel to drain fluid or administer a substance such as a medication.

Referring now to FIGS. 1-4, apparatus 20 for sealing, securing and adjusting the length of a flexible tube 9 is disclosed. The principal components of apparatus 20 are housing 1 and anchor 6. In one embodiment, housing 1 is made plastic but any other flexible material may be used as desired by one of skill in the art. Housing 1 has a sealing section 2, middle section 3 and opposing end 4. Housing 1 has a outer surface and an inner lumen 5. Lumen 5 is preferably a tubular channel configured to receive a flexible tube such as a catheter or cannula. The diameter of lumen 5 is preferably slightly greater than the diameter of the flexible tube which may vary. Middle section 3 has a reduced outer diameter as compared to the diameters of sealing section 1 and opposing end 4 contiguous to middle section 3. The reduced outer diameter of middle section 3 allows housing 1 to attach to anchor 6.

Referring to FIGS. 2-5, anchor 6 has base 8 and grip 7. In one embodiment, grip 7 extends upwardly perpendicular from base 8. In another embodiment, shown in FIG. 5, grip 7 extends upwardly at an angle 13 from base 8. Angle 13 is preferably an obtuse angle but may be an angle of any degree as desired by one of skill in the art. Grip 7 is configured to engage with middle section 3 of housing 1. Anchor 6 has two apertures 26 which allow anchor 6 to be secured to the skin of a recipient of a flexible tube such as catheter or cannula. Anchor 6 is secured to the recipient with sutures but any other method to secure anchor 6, such as adhesive, may be used as desired by one of skill in the art.

Figures 7, 8:
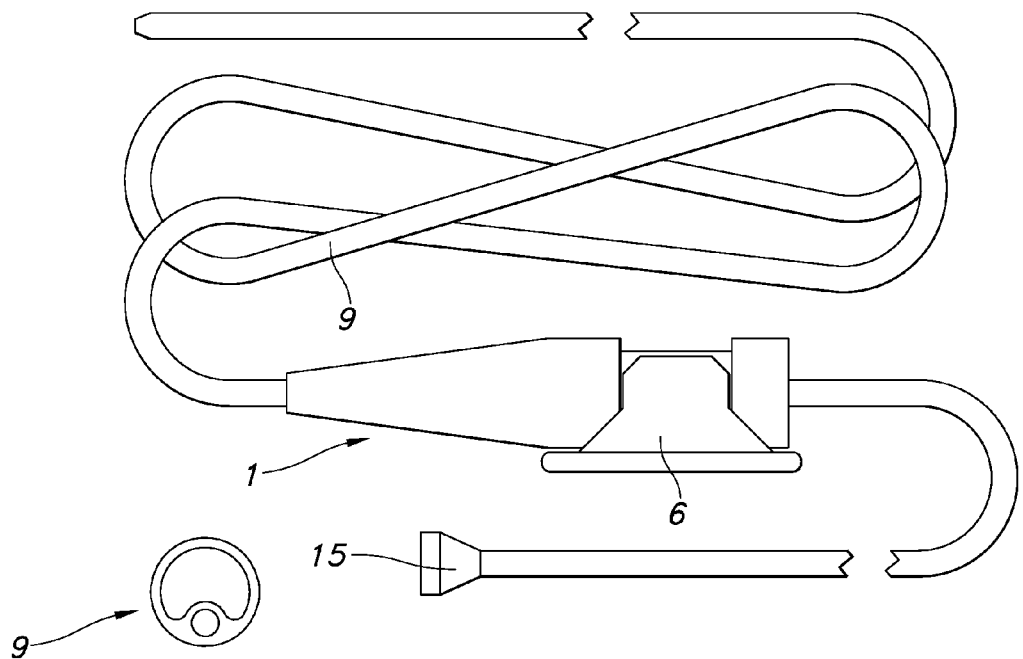
FIG. 7 is a schematic side view of an apparatus for sealing, securing and adjusting the length a flexible tube with a catheter or tube inserted therein.
FIG. 8 depicts a cross section of a flexible tube or catheter.

Referring to FIGS. 7-8, flexible tube 9 is preferably a catheter or cannula but any other flexible tube may be used as desired by one of skill in the art.

Figures 9, 10:
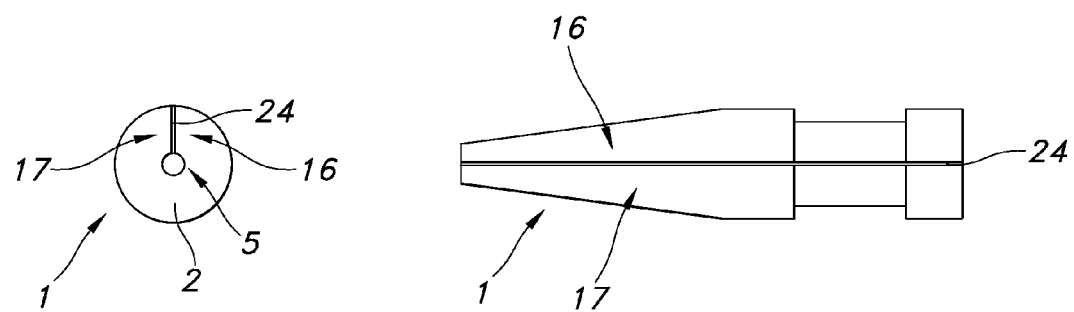
FIG. 9 is a schematic top view of a housing with abutted surfaces which define a slit.
FIG. 10 is a cross section of a sealing section of the housing.

Referring now to FIGS. 9-10, housing 1 has one pair of abutted surfaces 16 and 17 which define slit 24. Slit 24 extends from the outer surface of housing 1 to inner lumen 5. Slit 24 enables housing 1 to be slid onto tube 9.

Figure 6:
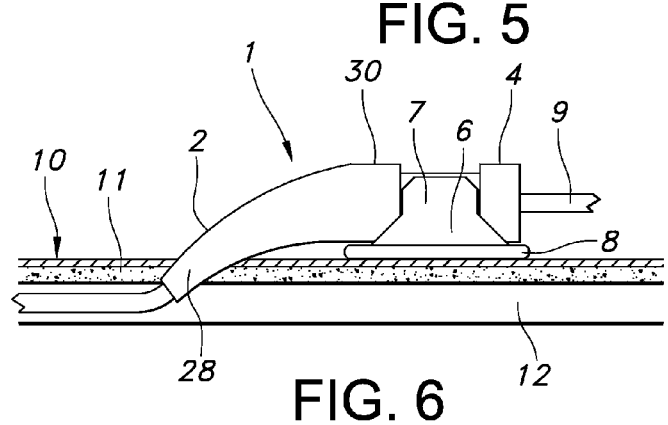
FIG. 6 is a schematic side view of an apparatus for sealing, securing and adjusting the length of a flexible tube secured to the skin of a recipient.
Figure 11:
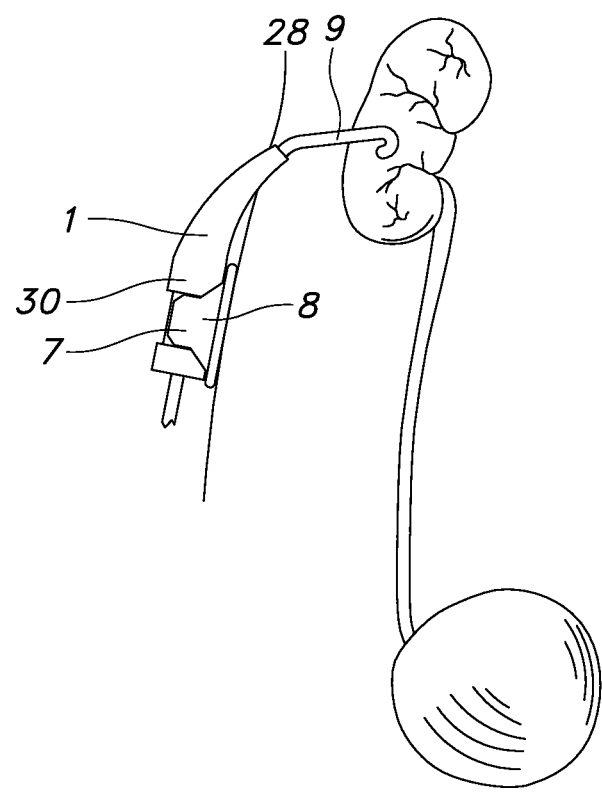
FIG. 11 is a schematic view of the apparatus attached to the body of a recipient of a catheter, wherein the catheter is inserted into an organ of the recipient.
Figure 12:
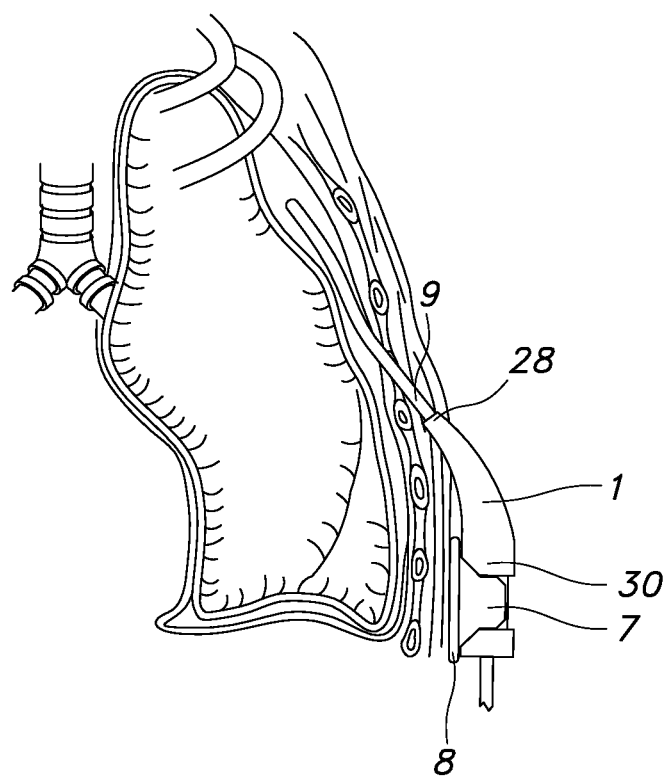
FIG. 12 is a schematic view of the apparatus attached to the body of a recipient of a tube or catheter wherein the tube is inserted into a body cavity of the recipient.

Referring now to FIGS. 6, 11-12, sealing section 2 has insertion end 28 and distal end 30. Distal end 30 is contiguous to middle section 3 of housing 1. Sealing section 2 is smooth tapered from distal end 30 to insertion end 28. In another embodiment, sealing section 2 is stepped tapered from distal end 30 to insertion end 28. Insertion end 28 is inserted into the tissue of a recipient of a tube thereby sealing the entry wound.

The cooperation of the surrounding tissue's natural elasticity and a tapered, smooth or stepped, sealing section 2 inserted into the insertion site provide a seal that will prevent contamination of or drainage from the insertion site.

In one embodiment, opposing end 4 is a hub receiver used to connect flexible tube 9 to a fluid supply. In another embodiment, shown in FIG. 7, hub receiver 15 is located on tube 9 away from housing 1. Hub receiver 15 is used to connect tube 9 to a fluid supply.

Referring again to FIG. 6, apparatus 20 is used to seal, secure and adjust the length of catheter 9 in arterial and venous applications. Tube or catheter 9 is inserted into vein 12. Tube 9 is inserted into housing 1 by way of slit 24 (not shown in FIG. 6). Insertion end 28 of sealing section 2 is slid down tube 9 to the insertion site and inserted into tissue 11. The entry of insertion end 28 into tissue 11 seals the insertion site. Middle section 3 of housing 1 is attached to anchor 6 by way of grip 7. Base 8 of anchor 6 is secured to skin 10 proximal to the insertion site by way of sutures (not shown) thereby securing catheter 9. The length of catheter 9 may be modified or adjusted as required until the tip position is in the desired location for therapeutic purposes.

Referring again to FIG. 11, apparatus 20 is used to seal, secure and adjust the length of catheter 9. In this application, apparatus 20 is used to seal, secure and adjust the length of a percutaneous nephrostomy catheter 9 inserted into a body organ. Tube or catheter 9 is inserted an organ. Catheter 9 is inserted into housing 1 by way of slit 24 (not shown in FIG. 11). Insertion end 28 of sealing section 2 is slid down catheter 9 to the insertion site and inserted into tissue of the recipient of catheter 9. The entry of insertion end 28 into the tissue seals the insertion site. Middle section 3 of housing 1 is attached to anchor 6 by way of grip 7. Base 8 of anchor 6 is secured to skin proximal to the insertion site by way of sutures (not shown) thereby securing catheter 9. The length of catheter 9 can be modified or adjusted as required until the tip position is in the desired location for therapeutic purposes.

Referring again to FIG. 12, apparatus 20 is used to seal, secure and adjust the length of tube 9. In this application, apparatus 20 is used to seal, secure and adjust the length of a chest tube 9 inserted into a body duct or cavity. Tube 9 is inserted into housing 1 by way of slit 24 (not shown in FIG. 12). Insertion end 28 of sealing section 2 is slid down tube 9 to the insertion site and inserted into tissue of the recipient of tube 9. The entry of insertion end 28 into the tissue seals the insertion site. Middle section 3 of housing 1 is attached to anchor 6 by way of grip 7. Base 8 of anchor 6 is secured to skin proximal to the insertion site by way of sutures (not shown) thereby securing catheter 9. The length of catheter 9 can be modified or adjusted as required until the tip position is in the desired location for therapeutic purposes.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the disclosed invention and equivalents thereof.

I claim:

1. A mounting apparatus for securing to an insertion site on a recipient patient, said apparatus including an implantable flexible tube for sealing within said insertion site, and said apparatus allowing for adjustably securing a length of said implanted tube at said insertion site, comprising:

a housing having a front end including a contoured, flexible sealing section, a middle anchor section, and a back end including a tube exit section, wherein said housing has an outer surface and an inner longitudinal lumen extending from said front end to said back end, wherein the lumen is configured to adjustably receive the tube therein, wherein said housing has at least one pair of abutted surfaces which define a slit which extends radially inwardly from said outer surface to said lumen such that said slit extends longitudinally from said front end to said back end, and an anchor having a base and a grip, wherein said grip extends upwardly from said base and wherein said grip is configured to engage said housing in the middle anchor section of said housing, and wherein said base secures to said insertion site;

wherein said housing is flexible to permit insertion of at least the front end thereof within said insertion site simultaneously with said implantable flexible tube.

2. The apparatus of claim 1 further comprising a flexible tube, wherein said flexible tube is a cannula.

3. The apparatus of claim 1 further comprising a flexible tube, wherein said flexible tube is a catheter.

4. The apparatus of claim 1 further comprising a flexible tube, wherein said flexible tube is a percutaneous nephrostomy catheter.

5. The apparatus of claim 1 further comprising a flexible tube, wherein said flexible tube is a chest tube.

6. The apparatus of claim 1 wherein said sealing section has an insertion end and a distal end, wherein said distal end is contiguous to said middle section of said housing, wherein said sealing section is tapered from said distal end to said insertion end.

7. The apparatus of claim 6 wherein said taper is smooth.

8. The apparatus of claim 6 wherein said taper is stepped.

9. The apparatus of claim 1 wherein said opposing end is a hub receiver.

10. The apparatus of claim 1 wherein said base has two apertures.

11. The apparatus of claim 1 wherein said grip extends upwardly perpendicular from said base.

12. The apparatus of claim 1 wherein said grip extends upwardly from said base at an angle greater than 90°.

13. The apparatus of claim 1 wherein said grip extends upwardly from said base at an angle less than 90°.

14. A method for using the apparatus of claim 1 to seal, secure and adjust the length of a flexible tube having a tip, wherein said method comprises the steps:

a. preparing an insertion site of a recipient of the flexible tube, wherein said insertion site includes tissue under said recipient's skin;

b. inserting said flexible tube into said insertion site;

c. guiding said tube to a desired location within the recipient;

d. passing said tube into the lumen of the housing by way of the slit;

e. inserting the sealing section of the housing into the insertion site, wherein at least said front end of said sealing section is in contact with said tissue under said recipient's skin;

f. attaching said middle section of said housing into said grip of said anchor;

g. affixing said anchor proximate to said insertion site, and h. modifying the length of the flexible tube as required until the tip of the tube is in the desired location within the recipient.

* * * * *